United States Patent [19]

Yelland

[11] Patent Number: 5,344,966
[45] Date of Patent: Sep. 6, 1994

[54] HYDROGENATION OF PHENYLPHOSPHONIC ACID

[75] Inventor: Michael Yelland, Rossendale, England

[73] Assignee: Imperial Chemical Industries PLC, London, England

[21] Appl. No.: 118,501

[22] Filed: Nov. 5, 1992

Related U.S. Application Data

[63] Continuation of Ser. No. 607,790, Oct. 26, 1990, abandoned, which is a continuation of Ser. No. 281,488, Dec. 8, 1988, abandoned.

[30] Foreign Application Priority Data

Dec. 16, 1987 [GB] United Kingdom ............... 8729341

[51] Int. Cl.$^5$ .............................................. C07F 9/38
[52] U.S. Cl. .......................................... 562/8; 562/11
[58] Field of Search ...................................... 562/8, 11

[56] References Cited

U.S. PATENT DOCUMENTS 3,754,085  8/1973  Christensen et al. ............... 562/11
4,212,990  7/1980  Yasuhara et al. ................... 560/241

FOREIGN PATENT DOCUMENTS 321106  6/1989  European Pat. Off. ............... 562/8

Primary Examiner—Joseph E. Evans
Attorney, Agent, or Firm—Paul L. Sharer

[57] ABSTRACT

A cycloalkyl phosphorus compound is obtained by the catalytic hydrogenation of a substituted or unsubstituted aryl phosphonic acid using a heterogeneous catalyst which is a Group VIII metal on carbon. The hydrogenation is preferably effected in water. The catalyst can be ruthenium or carbon. When phenylphosphonic acid is used as the starting material, a yield of about 95% of essentially pure cyclohexylphosphonic acid can be obtained.

11 Claims, No Drawings

HYDROGENATION OF PHENYLPHOSPHONIC ACID

This is a continuation, of co-pending application Ser. No. 07/607,790 filed on Oct. 26, 1990 now abandoned, which is itself a continuing application of, now abandoned, Ser. No. 07,281,488 filed on Dec. 8, 1988.

The present invention relates to a process for the production of cycloalkyl phosphorus compounds, particularly cyclohexyl phosphonic acid.

Organic phosphorus compounds have a wide range of uses, for example as plasticisers for vinyl chloride polymers and copolymers, as stabilisers for olefin polymers, as additives during the production of polymers and in agrochemical applications. Phosphonic acids such as cycloalkyl phosphonic acids can be used, inter alia, to increase the molecular weight of pre-formed polyamides (GB 1092845), or to improve the dye affinity of polyamide fibres (FR 1512185) or for the production of organophosphorus-vanadium compounds which can be used as fuel combustion additives, particularly diesel fuel additives (U.S. Pat. No. 3,290,342) or as a cross-linking additive for acrylic copolymers which contain epoxy groups (U.S. Pat. No. 4,241,196).

GB 707961 describes the preparation of organic phosphonyl dichlorides by the reaction of an organic chloride which may be, inter alia, a cycloalkyl chloride, with phosphorus trichloride in the presence of anhydrous aluminium chloride followed by controlled hydrolysis. However, it is indicated that if hydrolysis is not controlled and an excess of water is used, the final product is the corresponding phosphonic acid. Whatever degree of hydrolysis is used, hydrogen chloride is formed as a by-product. The hydrogen chloride is a corrosive material under the conditions used and has been found to cause a rapid deterioration of the equipment used with the need for regular replacement of the equipment.

An alternative procedure involves the catalytic hydrogenation of aromatic compounds using a rhodium-on-alumina catalyst (J. American Chemical Society, 77 (1955) pages 4262 and 4263). The procedure described is effected in ethyl alcohol and uses phenylphosphonic acid and the catalyst in essentially equal weight proportions. The yield of cyclohexylphosphonic acid is reported as 86%. However, the proportion of catalyst used is commercially unattractive in view of the high cost of the catalyst. We have found that by using a different catalyst it is possible to achieve a higher yield of the desired cycloalkyl product using a lower proportion of the catalyst.

According to the present invention there is provided a process which comprises hydrogenating a substituted or unsubstituted aryl phosphonic acid in the presence of a liquid medium and a heterogenerous catalyst which is a Group VIII metal on carbon.

The substituted or unsubstituted aryl group is typically a phenyl group which may be substituted with at least one hydrocarbyl substituent which is typically an alkyl group containing up to six carbon atoms. Alternatively the substituent may be an amino-group, for example a primary amino group as in 4-aminophenylphosphonic acid. Other substituents may be present but it is desirable that such other substituents are not hydrogenated under the reaction conditions or are not such as to interfere with the hydrogenation. The process of the present invention is conveniently effected using phenylphosphonic acid.

The liquid medium is preferably one in which at least the phosphonic acid product is soluble under the reaction conditions and it is especially preferred that both the product and the reactant are soluble in the liquid medium. The liquid medium is very conveniently water but any other liquid medium in which at least the phosphonic acid product is soluble may be used. However, it is preferred to avoid the use of alcohols since these are liable to react with the phosphonic acid to form esters thus reducing the yield of the desired acid. The use of a liquid medium in which the phosphonic acid product is soluble is preferred to facilitate the removal of the catalyst from the reaction mixture on completion of the reaction.

The heterogeneous catalyst may contain platinum or palladium and we have obtained good results using a ruthenium on carbon catalyst. The catalyst preferably contains at least 1% by weight of the Group VIII metal. Typically the catalyst contains not more than 10% by weight of the Group VIII metal and especially is about 5% by weight. The catalyst is used in an amount which is typically from 1% up to 10% by weight of the weight of the aryl phosphonic acid, especially about 5% by weight of the aryl phosphonic acid.

The hydrogenation is preferably effected at an elevated temperature, for example at least 50° C. and typically at least 100° C. A temperature in excess of 200° C. is generally not required and the temperature preferably does not exceed 150° C.

The pressure should be such that the liquid medium remains liquid at the reaction temperature. It is generally preferred to use an elevated pressure which is conveniently attained by the addition of the hydrogen used to effect the hydrogenation. The pressure is typically at least 0.2 $MNm^{-2}$ absolute and in general does not exceed 10 $MNm^{-2}$ absolute. The pressure is preferably in the range from 1 up to 5 $MNm^{-2}$ absolute.

The hydrogenation is effected in the substantial, preferably complete, absence of oxygen or any other gas which is liable to form an explosive mixture with hydrogen. The hydrogenation can be effected in the presence of an inert gas but it is convenient to effect the hydrogenation in the presence of an atmosphere which is predominantly, or completely, hydrogen.

During the hydrogenation, the reaction mixture is agitated. To aid the reaction, the hydrogen is added by being bubbled through the reaction mixture. The progress of the reaction can be monitored by measuring the up-take of hydrogen, for example using a Peteric gas flow controller and a Bourdon tube gauge. When the up-take of hydrogen ceases, or has essentially ceased, the hydrogenation is complete. Alternatively, the progress of the reaction may be followed using high performance liquid chromatography to measure the level of aromatic species in the reaction medium. The disappearance of the aromatic species indicates completion of the reaction. Completion of the reaction is dependent on the reaction conditions and typically takes from 1 up to 15 hours.

When the reaction is complete the reaction mixture is allowed to cool and the pressure is reduced. The catalyst is removed from the reaction mixture by any suitable technique, for example by filtration. The reaction product may then be recovered by evaporating off the liquid medium. The solid residue is the desired product and, if desired, can be purified by any suitable technique such as crystallisation. However, using the process of the present invention the product obtained can be of a high degree of purity and further purification is generally unnecessary.

The process of the present invention is more fully described in the following non-limiting example.

EXAMPLE

Into a stainless steel autoclave having a capacity of 1 dm$^3$ and fitted with a magnetically operated turbine agitator were placed 500 cm$^3$ of distilled water. 63.2 g of phenylphosphonic acid were added to the water and 3.2 g of 5% ruthenium on carbon were then added. The autoclave was then sealed and evacuated, and the pressure was released with nitrogen. The autoclave was again evacuated and the pressure released with nitrogen and finally the autoclave was evacuated and pressurised to 0.79 MNm$^{-2}$ absolute (100 psi gauge) with hydrogen. The contents of the autoclave were stirred at 1000–1100 r.p.m. and the autoclave and its contents were heated to 120° C. At a temperature of about 95° C., the pressure started to fall and was then increased to 1.48 MNm$^{-2}$ absolute (200 psi gauge), and maintained at this pressure until the reaction was judged to be complete.

On attaining a temperature of 120° C., stirring was continued and the temperature was maintained at 120° C. whilst passing hydrogen into the autoclave to maintain the pressure at 1.48 MNm$^{-2}$ absolute. After eight hours the uptake of hydrogen had essentially ceased and the reaction was then judged to be complete. Heating was terminated and the contents of the autoclave were allowed to cool whilst continuing to stir. When the mixture had cooled to 90°–95° C., the excess hydrogen was vented off and the mixture was screened (filtered) to recover the catalyst.

The filtrate was then evaporated to dryness to give 62.3 g (95% of theory) of cyclohexylphosphonic acid having a melting point of 166°–167° C., which was undepressed when effecting a mixed melting point with an authentic sample of cyclohexylphosphonic acid. The product was also characterised by its infra red spectrum. By high performance liquid chromatography unreacted phenylphosphonic acid could not be detected in the product indicating the phenylphosphonic acid level to be less than 0.03% by weight. No other by-products could be detected in the cyclohexylphosphonic acid reaction product.

I claim:

1. A process for producing a cycloalkyl phosphonic acid which comprises hydrogenating a phenyl phosphonic acid optionally substituted with an amino-group or at least one alkyl group containing from 1 to 6 carbon atoms in the presence of a liquid medium in which the phosphonic acid reaction product is soluble under the reaction conditions and which is not reactive with the phosphonic acid and a heterogeneous catalyst which is a Group VIII metal on carbon.

2. The process of claim 1 wherein the liquid medium is water.

3. The process of claim 1 wherein the heterogeneous catalyst is ruthenium on carbon.

4. The process of claim 1 wherein the catalyst contains at least 1%, and not more than 10% by weight of the Group VIII metal.

5. The process of claim 1 wherein the catalyst is used in an amount of from 1% up to 10% by weight of the substituted or unsubstituted phenyl phosphonic acid.

6. The process of claim 1 which is effected at a temperature of at least 50° C. and not in excess of 200° C.

7. The process of claim 1 which is effected at a hydrogen pressure of at least 0.2 MNm$^{-2}$ absolute and not exceeding 10 MNm$^{-2}$.

8. The process of claim 1 wherein the Group VIII metal is selected from the group consisting of platinum, palladium and ruthenium.

9. A process which comprises hydrogenating a phenyl phosphonic acid optionally substituted with an amino-group or at least one alkyl group containing from 1 to 6 carbon atoms in the presence of water and a heterogeneous catalyst which is a Group VIII metal on carbon wherein the catalyst contains at least 1% and not more than 10% by weight of the group VIII metal.

10. The process of claim 1 in which the phenylphosphonic acid is optionally substituted with at least one alkyl group containing from 1 to 6 carbon atoms.

11. A process for producing cyclohexyl phosphonic acid comprising hydrogenating phenylphosphonic acid in the presence of a liquid medium in which the phosphonic acid reaction product is soluble under the reaction conditions and which is not reactive with the phosphonic acid and a heterogeneous catalyst which is a Group VIII metal on carbon.

* * * * *